(12) United States Patent
Okada

(10) Patent No.: US 6,198,482 B1
(45) Date of Patent: Mar. 6, 2001

(54) SYSTEM CONTROLLER FOR ANALYZER

(75) Inventor: Kohji Okada, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/134,871

(22) Filed: Aug. 17, 1998

(30) Foreign Application Priority Data

Aug. 29, 1997 (JP) ................................. 9-249741

(51) Int. Cl.$^7$ ............................ G06F 3/00; G06F 17/00
(52) U.S. Cl. .................. 345/353; 345/356; 345/357; 345/970; 702/127; 702/183
(58) Field of Search ................... 345/353, 356, 345/357, 970, 965, 967, 347, 349; 702/127, 182, 183, 189

(56) References Cited

U.S. PATENT DOCUMENTS

| | | | |
|---|---|---|---|
| 4,873,623 | * 10/1989 | Lane et al. | 700/83 |
| 5,611,059 | * 3/1997 | Benton et al. | 345/326 |
| 5,737,727 | * 4/1998 | Lehmann et al. | 705/7 |
| 5,774,667 | * 6/1998 | Garvey et al. | 709/222 |
| 5,896,138 | * 4/1999 | Riley | 345/440 |
| 5,909,372 | * 6/1999 | Thybo | 700/83 |

* cited by examiner

*Primary Examiner*—Raymond J. Bayerl
*Assistant Examiner*—Cuong T. Thai
(74) *Attorney, Agent, or Firm*—Armstrong, Westerman, Hattori, McLeland & Naughton

(57) ABSTRACT

A parameter display part including a single upper-hierarchical parameter screen displaying only a selected parameter and a number of lower-hierarchical parameter screens corresponding to respective units displaying all parameters for the respective units, and providing switchable display capability. When selecting a parameter to be displayed on the upper-hierarchical parameter screen, moving the cursor to the parameter on any of the lower-hierarchical parameter screens and pressing the function key to select a display, the selected parameter is displayed on the upper-hierarchical parameter screen. When the parameter is selected again, the function key is pressed, and the display on the upper-hierarchical parameter screen is canceled.

7 Claims, 5 Drawing Sheets

Fig. 3A (a)

```
ANALYSIS FILE                          FILE      0
    PUMP (B. GE)              DET. A
T. FLOW    1.000  mL/min    WAVE      254   nm
B. CONC    50.0   %         AUXRNG    2
P. MAX     20.0   MPa       RESP      2

DET. B

MONITOR
A. PRES    9.8   MPa
B. PRES    9.8   MPa
C. PRES    9.8   MPa
                              OVEN
                            OVEN.T    40°C

READY
                                    15:00:00
```

Fig. 3B (b)

```
ANALYSIS FILE                          FILE      0
 * * * PUMP (LP. SE) * * *
*T. FLOW    ▨00  mL/min    P. MIN     0    MPa
*B. CONC    60.0   %        LPGE. M    0
 C. CONC    0.0    %        B. CURV    0
 D. CONC    0.0    %        C. CURV    0
 B. FLOW    3.000 mL/min    D. CURV    0
 C. FLOW    4.000 mL/min    PASV       0
*P. MAX     9.8   MPa       PBSV       0
                            PCSV       0

*                                  READY
 SEL|DEL              EXIT          15:00:00
```

CURSOR

SYSTEM CONTROLLER FOR ANALYZER

BACKGROUND OF THE INVENTION

1. Field of the Invention

The present invention relates to the system controller of any of the following analyzers: a high-speed liquid chromatograph, a gas chromatograph, a liquid chromatograph/mass spectrometer or a gas chromatograph/mass spectrometer.

2. Description of the Related Art

A high-speed liquid chromatograph comprises some of the following units: a feed pump, a detector, an automatic sampler and a column oven, all of which require parameter settings. Other analyzers also comprise some units requiring parameter settings. Such analyzers prepare a number of parameters to control these units, in order to cope with various analysis conditions. The analyzers comprise a system controller, which controls these units through these parameters. The system controller displays these parameters on a display.

A conventional system controller immovably displays these parameters on the same position of the display, and displays all available parameters on a single screen.

While there are many available parameters, those changed in daily analysis are extremely limited. When changing a portion of the parameters, many unnecessary parameters displayed on the display are so obstructive it takes time to search for the target parameter. If the parameter to be changed is displayed on a lower portion of the screen, it inconveniently takes time to move the cursor on the screen to select the parameter.

SUMMARY OF THE INVENTION

Accordingly, the object of the present invention is to make system controller parameter screens easier to view and easier to operate for the user, thereby eliminating any inconveniences.

The system controller for an analyzer, according to the present invention, comprises a parameter display part for displaying parameter conditions to control each unit, a parameter condition storage part, a parameter-input part, a parameter condition transmission part and a parameter input processing part. The parameter display part has an upper-hierarchical parameter screen displaying only the selected parameter(s) and a lower-hierarchical parameter screen displaying all parameters. The parameter condition storage part stores display/non-display modes on the upper-hierarchical parameter screen and parameter conditions of each parameter as data. The parameter-input part inputs the display/non-display modes on the upper-hierarchical parameter screen and the parameter conditions of each parameter. The parameter condition transmission part transmits the parameter conditions for each parameter to a corresponding unit. The parameter input processing part transmits data from the parameter input part to the parameter condition storage part, and transmits the data stored in the parameter storage part to the parameter display part and the parameter condition transmission part.

The lower-hierarchical parameter screen displays every parameter of all available units, and the upper-hierarchical parameter screen displays only the parameter(s) selected in the lower-hierarchical parameter screen. This parameter display part may have a single upper-hierarchical parameter screen and a number of lower-hierarchical parameter screens corresponding to respective units.

The parameter display part first displays the upper-hierarchical parameter screen. The displayed parameter screen can be switched by key operation. After selecting an arbitrary parameter on any of the lower-hierarchical parameter screens, the selected parameter is displayed on the upper-hierarchical parameter screen. The user can adjust the upper-hierarchical parameter screen displaying only the parameter(s) to be used in response to any desired analysis by selecting one or a plurality of parameters in any of the lower-hierarchical parameter screens, which then enables the user to bring the parameter screen of the system controller to a usable state.

The upper-hierarchical parameter screen of the system controller according to the present invention displays only the frequently changing parameter(s), whereby the parameter screen can be rendered easier to view and easier to operate for the user, thus eliminating any inconveniences.

The foregoing along with other objects, features, aspects and advantages of the present invention will become more apparent from the following detailed description of the present invention when taken in conjunction with the accompanying drawings.

BRIEF DESCRIPTION OF THE DRAWINGS

FIGS. 3(A) and 3(B) show exemplary upper- and lower-hierarchical parameter screens of the embodiment.

DESCRIPTION OF THE PREFERRED EMBODIMENT

Figure 1:
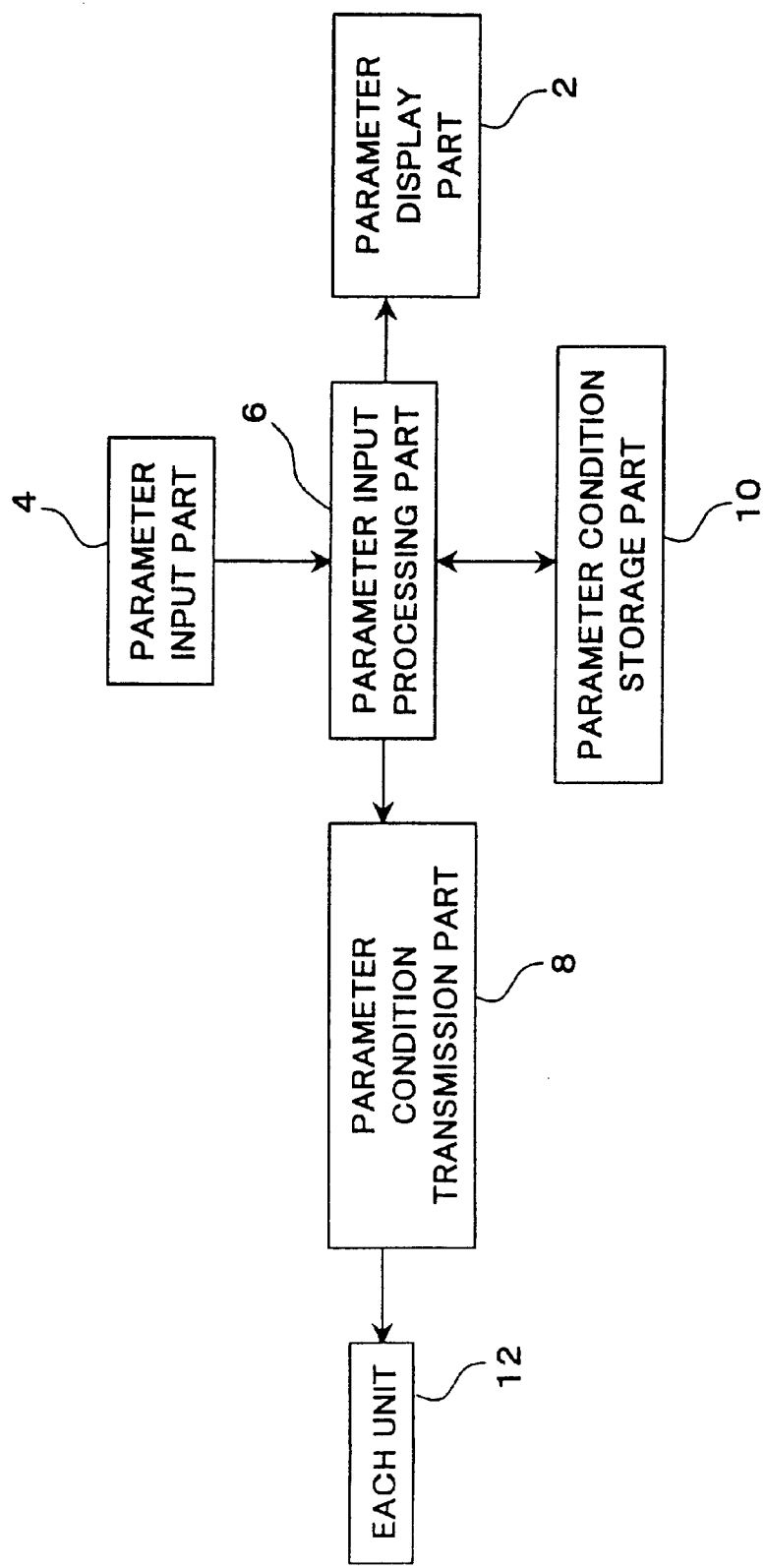
FIG. 1 is a block diagram showing the present invention.

FIG. 1 schematically shows a system controller for an analyzer according to the present invention. The parameter display part 2 is adapted to display parameter conditions for controlling each unit. The parameter display part 2 comprises a single upper-hierarchical parameter screen displaying only the selected parameter(s) and a number of lower-hierarchical parameter screens, which correspond to respective units and display all parameters for these respective units. These parameter screens are switched by key operation, to be displayed.

The parameter-input part 4 is adapted to input data of information as to whether or not each parameter is displayed on the upper-hierarchical parameter screen and the parameter conditions thereof.

The parameter condition storage part 10 is adapted to store the data inputted through the parameter-input part 4.

The parameter condition transmission part 8 transmits the parameter conditions for each parameter to a corresponding unit 12.

The parameter input processing part 6 transmits the data from the parameter input part 4 to the parameter condition storage part 10, and further transmits the data stored in the parameter storage part 10 to the parameter display part 2 and the parameter condition transmission part 8.

Figure 2:
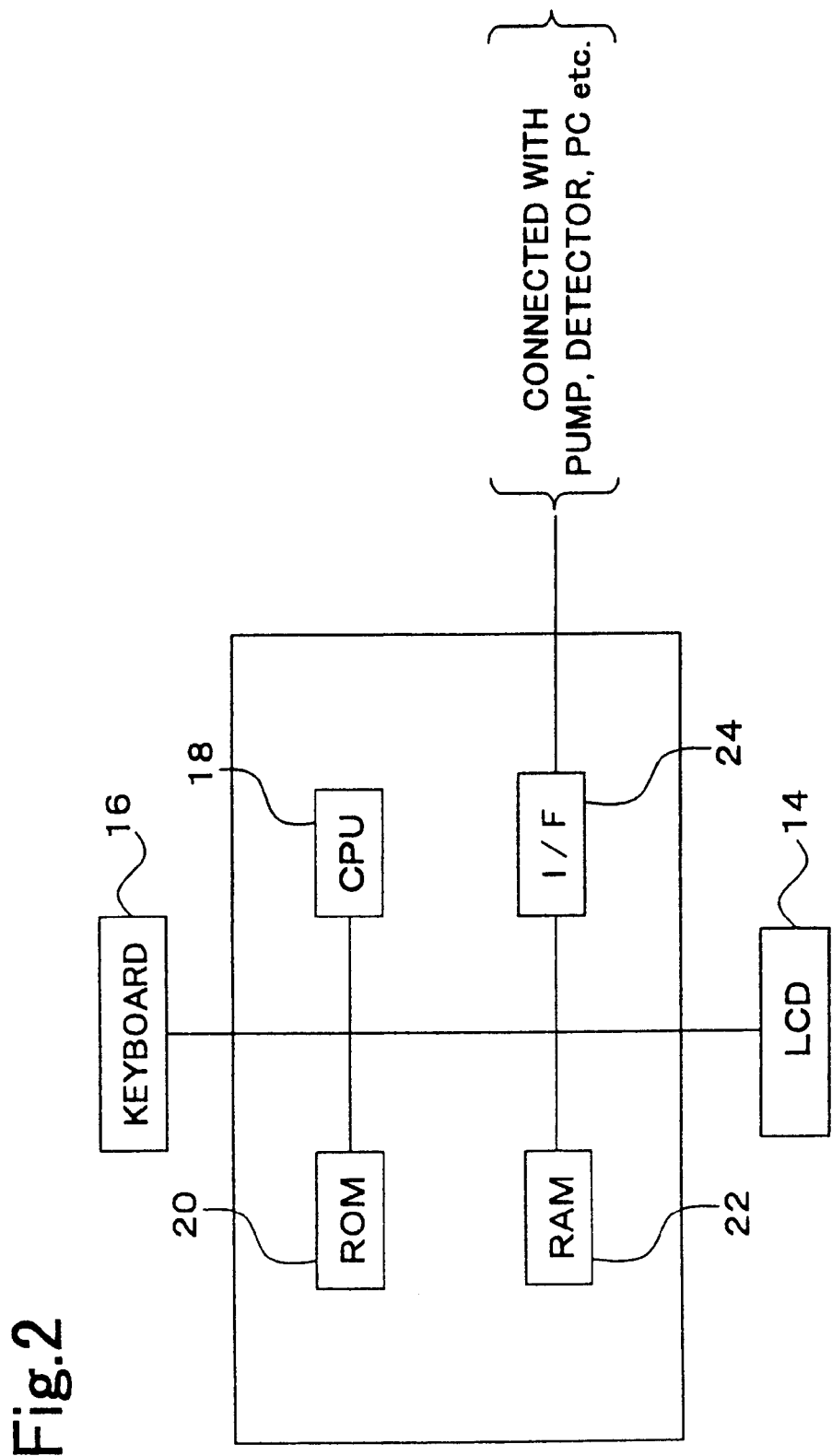
FIG. 2 is a block diagram showing an embodiment of the present invention.

FIG. 2 schematically shows an embodiment of the present invention, which is applied to a high-speed liquid chromatograph. The LCD (liquid crystal display unit) 14 is provided for the displaying of parameter conditions to control respective units. The LCD 14 switchably displays an upper-hierarchical parameter screen displaying only a selected parameter and lower-hierarchical parameter screens displaying all parameters for respective units. The keyboard 16 is provided to input parameter conditions and display/non-display modes on the upper-hierarchical parameter screen. The CPU 18 and the ROM 20 process the data inputted from the keyboard 16. The RAM 22 stores the data inputted from the keyboard 16 and processed in the CPU 18 and the ROM 20. The data processed in the CPU 18 and the ROM 20 are transmitted to units such as a pump and a detector through an interface 24, so that the respective units change conditions on the basis of signals thereof. The signals detected by the detector are processed in the CPU 18 and the ROM 20, to be thereafter transmitted to an external PC (personal computer).

Describing the relation between FIGS. 1 and 2, the LCD 14 shown in FIG. 2 implements the parameter display part 2 shown in FIG. 1, the CPU 18 and the ROM 20 implement the parameter input processing part 6, the RAM 22 implements the parameter condition storage part 10, and the interface 24 implements the parameter condition transmission part 8.

FIG. 3A shows an exemplary upper-hierarchical parameter screen (a) and FIG. 3B shows an exemplary lower-hierarchical parameter screens (b). The lower-hierarchical parameter screen (b) displays all parameters of each unit. The screen (b) in FIG. 3B, for example, displays all parameters of a pump unit Such a screen (b) is prepared for every unit. On the other hand, the upper-hierarchical parameter screen (a) collects and displays only the parameter(s) selected in these lower-hierarchical screens (b).

Figure 4:
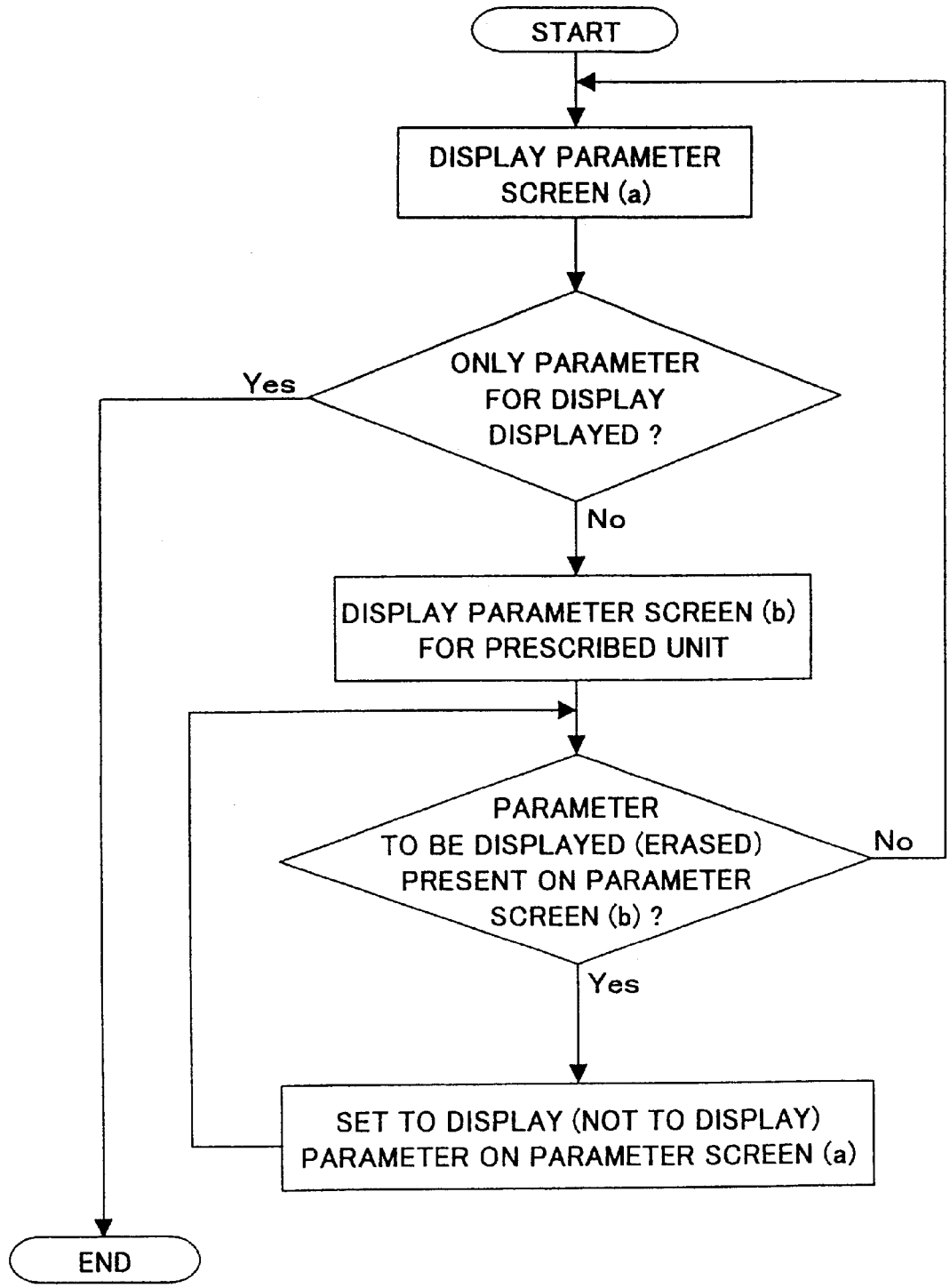
FIG. 4 is a flow chart showing an operation procedure in the selection or cancellation of a parameter displayed on the upper-hierarchical screen of the embodiment.

FIG. 4 is a flow chart showing an operation procedure in the selection or cancellation of parameters displayed on the upper-hierarchical parameter screen (a). The operation procedure for parameter selection or cancellation is now described with reference to FIGS. 3A, 3B and 4. The following description is made with reference to pump parameters.

Parameter screen (a) refers to the upper-hierarchical parameter screen (FIG. 3(A)) displaying only frequently changing parameters selected by the user among the parameters of each unit. Parameter screen (b) refers to the lower-hierarchical parameter screen (FIG. 3(B)) which is present for each unit to display all parameters changeable in the unit.

When selecting a parameter screen from a menu screen, screen (a) is displayed. When screen (a) already displays only the parameters to be displayed, the parameter selection is finished.

If screen (a) displays no parameters to be displayed or parameters not to be displayed, the user presses the display screen switching key to display screen (b) of a unit (a pump in this case) including the parameters. The user finds out the parameters, to be displayed or erased on screen (a), on screen (b), and moves the cursor to the parameters on screen (b). At this time, the user presses the function key "SEL/DEL" on the lower left of screen (b) to select a display.

Selection marks "*" are displayed on the left sides of the parameters, which are selected to be displayed on screen (a), on screen (b). When the user moves the cursor to the parameters and presses the function key "SEL/DEL" again, the selection is canceled, the display on screen (a) is also canceled and the display of the selection marks "*" is erased. It is assumed here that "T. FLOW", "B. CONC" and "P. MAX" are selected.

After completing the selection of all necessary parameters on screen (b), the user presses the display screen-switching key to return the display to screen (a). Consequently, only "T. FLOW", "B. CONC" and "P. MAX" selected on screen (b) are displayed on the pump parameter display part of screen (a). Thus, the parameter selection is finished.

Figure 5:
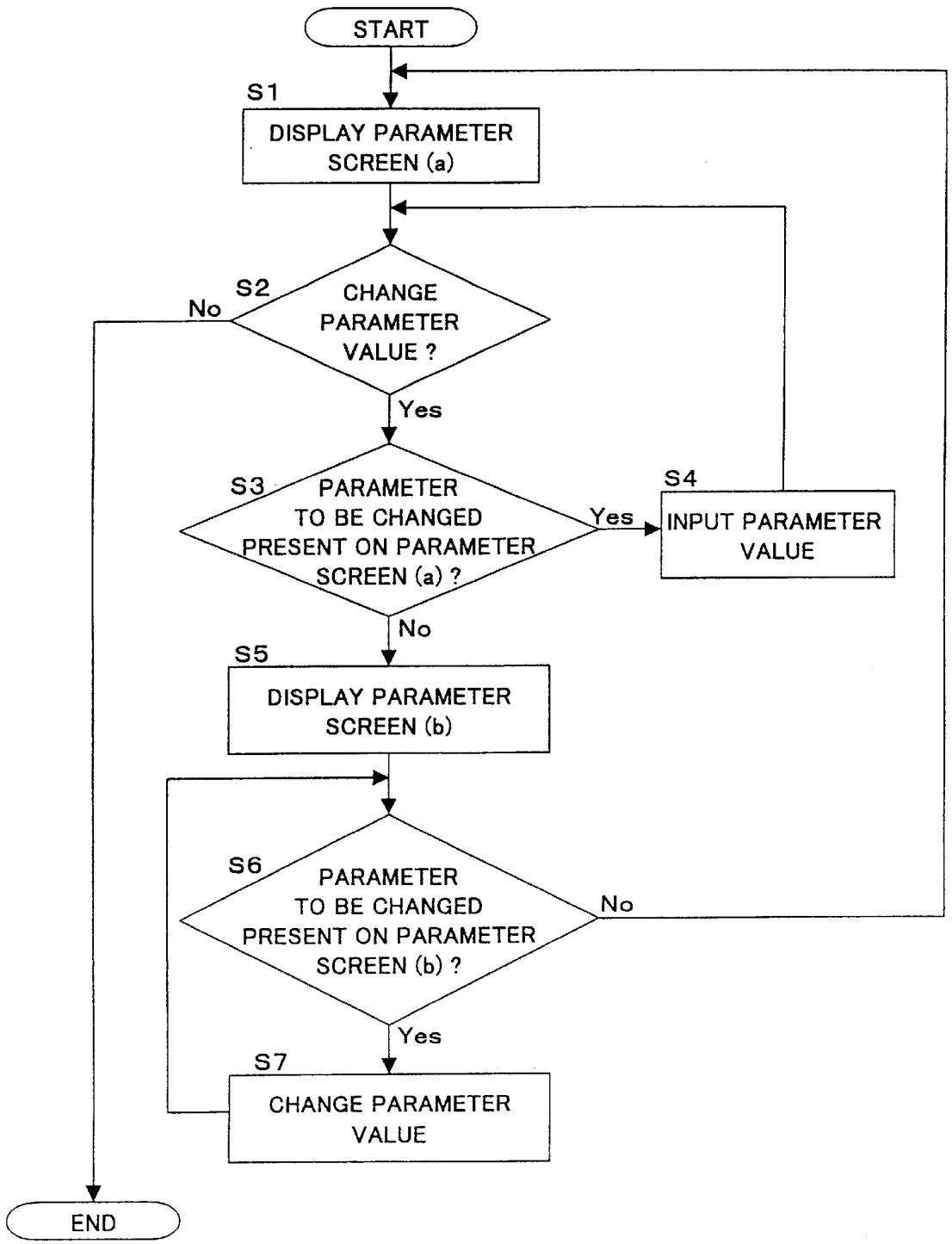
FIG. 5 is a flow chart showing a parameter set procedure of the embodiment

FIG. 5 is a flow chart showing a parameter set procedure. The parameter screens (a) and (b) are identical to those in FIGS. 3A and 3B. The parameter set procedure is now described with reference to FIG. 5.

When the user selects a parameter screen from the menu screen, screen (a) is displayed (S1). If there is no changing of the parameter value, the parameter set procedure is finished (S2).

However, if there is changing of the parameter value, the user confirms whether or not the parameter to be changed is present on screen (a) (S3). The user changes the parameter value if the parameter is present (S4), and the parameter set procedure is finished if there are no other parameter values to be changed (S2).

If there are no parameters to be changed on screen (a), the user presses the display screen switching key to display screen (b) including the parameter to be changed (S5), and confirms whether or not the parameter to be changed is present on screen (b) (S6). The user changes the parameter value if the parameter is present (S7), and he presses the display screen-switching key to return to screen (a) (S6→S1) if no parameter is present. If no other parameters are to be changed, the parameter set procedure is finished (S2).

In the case of changing the parameter, this can be done by repeating the procedure of S2→S3→S4 if the parameter to be changed is present on screen (a). However, if the parameter to be changed is not present on screen (a), this must be done by repeating the procedure of S1→S2→S3→S5→S6→S7→S6→S1 which is more complicated. Therefore, the parameter to be changed in daily analysis is preferably displayed on screen (a) in advance.

Although the present invention has been described and illustrated in detail, it is clearly understood that the same is by way of illustration and example only, and is not to be taken by way of limitation as the spirit and scope of the present invention is limited only by the terms of the appended claims.

What is claimed is:

1. A system controller for an analyzer the system including a plurality of units to be controlled, comprising:

a parameter display part displaying parameter conditions for the controlling of said plurality of units with an upper-hierarchical parameter screen displaying only the selected parameter(s) for all of said plurality of units and at least one lower-hierarchical parameter screen displaying all parameters;

a parameter condition storage part storing display/non-display modes for each said parameter on said upper-hierarchical parameter screen and parameter conditions thereof as data;

a parameter input part inputting said display/non-display modes for each said parameter and said parameter conditions;

a parameter condition transmission part transmitting said parameter conditions for each said parameter to corresponding said unit; and a parameter input processing part transmitting data from said parameter input part to said parameter condition storage part, and transmitting said data stored in said parameter condition storage part to said parameter display part and said parameter condition transmission part.

2. The system controller for an analyzer in accordance with claim 1, wherein said upper-hierarchical parameter screen displays only a parameter selected on the said lower-hierarchical parameter screen.

3. The system controller in accordance with claim 2, being adapted to select and cancel said parameter displayed on said upper-hierarchical parameter screen by selecting said parameter on said lower-hierarchical parameter screen with the cursor and pressing the prescribed key.

4. The system controller for an analyzer in accordance with claim 2, wherein
a selection mark is applied to the said parameter, which is selected and displayed on said upper-hierarchical parameter screen, on said lower-hierarchical parameter screen.

5. The system controller for an analyzer in accordance with claim 1, wherein said parameter display part comprises one said upper-hierarchical parameter screen and a number of lower-hierarchical parameter screens corresponding to each of said respective units, for displaying any of said parameter screens.

6. The system controller for an analyzer in accordance with claim 5, wherein the display of the any said parameter screen is switchable by key operation.

7. The system controller in accordance with claim 5, wherein said parameter display part first displays said upper-hierarchical parameter screen.

* * * * *